(12) United States Patent
Ibañez Ballesteros et al.

(10) Patent No.: US 11,589,750 B2
(45) Date of Patent: Feb. 28, 2023

(54) METHOD FOR OBTAINING NEAR-INFRARED SPECTROSCOPY CEREBRAL SIGNAL

(71) Applicant: NEWMANBRAIN, S.L., Elche (ES)

(72) Inventors: Joaquin Ibañez Ballesteros, Alicante (ES); Sergio Molina Rodriguez, Torrevieja (ES); Carlos Belmonte Martinez, San Juan de Alicante (ES)

(73) Assignee: NEWMANBRAIN, S.L., Elche (ES)

( * ) Notice: Subject to any disclaimer, the term of this patent is extended or adjusted under 35 U.S.C. 154(b) by 0 days.

(21) Appl. No.: 17/720,914

(22) Filed: Apr. 14, 2022

(65) Prior Publication Data
US 2023/0026344 A1    Jan. 26, 2023

(30) Foreign Application Priority Data

Jul. 23, 2021  (EP) .................................. 21382675
Aug. 3, 2021  (EP) .................................. 21382733

(51) Int. Cl.
*A61B 5/00*   (2006.01)

(52) U.S. Cl.
CPC .......... *A61B 5/0082* (2013.01); *A61B 5/0075* (2013.01); *A61B 5/4035* (2013.01);
(Continued)

(58) Field of Classification Search
CPC ... A61B 5/0082; A61B 5/0075; A61B 5/4035; A61B 5/4064; A61B 5/4088; A61B 5/72;
(Continued)

(56) References Cited

U.S. PATENT DOCUMENTS 6,862,534 B2 *   3/2005   Sterling ............. A61B 5/14532
                                                    702/22
9,970,955 B1 *   5/2018   Homyk ................ A61B 5/0261
(Continued)

OTHER PUBLICATIONS

Saager "Measurement of layer-like hemodynamic trends in scalp and cortex: implications for physiological baseline suppression in functional near-infrared spectroscopy" Journal of Biomedical Optics, Jun. 2008 (Year: 2008).*

(Continued)

*Primary Examiner* — Oommen Jacob
(74) *Attorney, Agent, or Firm* — Sughrue Mion, PLLC

(57) ABSTRACT

A method for obtaining a near-infrared spectroscopy (fNIRS) cerebral signal in a subject includes: placing a near-infrared emitter and respective proximal and distal near-infrared detectors on a skin of a head of a subject; during a baseline recording stage with the subject in resting-state, record near-infrared signals, the recorded signals including a baseline deep-signal and a baseline shallow-signal; calculate a scaling factor between amplitudes of the baseline deep-signal and the baseline shallow-signal at a given task-frequency; with the subject undergoing a cyclic cerebral stimulation at the task-frequency during a stimulation recording stage, record near-infrared signals, the recorded signals comprising a shallow-signal and a deep-signal; and applying the scaling factor to the shallow-signal, calculating the cerebral signal at the task-frequency as a difference between the deep-signal and the scaled shallow-signal, at the task-frequency.

16 Claims, 4 Drawing Sheets

(52) U.S. Cl.
CPC .......... *A61B 5/4064* (2013.01); *A61B 5/4088* (2013.01); *A61B 5/72* (2013.01)
(58) Field of Classification Search
CPC .......... A61B 5/00; A61B 5/031; A61B 5/369; A61B 5/14553
See application file for complete search history.

(56) References Cited

U.S. PATENT DOCUMENTS

| | | | |
|---|---|---|---|
| 11,016,567 B1 | 5/2021 | Nour et al. | |
| 2009/0209836 A1* | 8/2009 | Niwayama | A61B 5/14551 600/324 |
| 2015/0223694 A1* | 8/2015 | Funane | A61B 5/4064 600/407 |
| 2016/0278643 A1* | 9/2016 | Kiguchi | A61B 5/4064 |
| 2016/0361017 A1* | 12/2016 | Busch, Jr. | A61B 5/7282 |
| 2019/0336077 A1* | 11/2019 | Kuhn | A61B 5/14546 |
| 2021/0076958 A1* | 3/2021 | Pierro | A61B 5/031 |

OTHER PUBLICATIONS

Hu "Reduction of trial-to-trial variability in functional near-infrared spectroscopy signals by accounting for resting-state functional connectivity" Journal of Biomedical Optics, Jan. 2013 (Year: 2013).*
Saager, "Two-detector Corrected Near Infrared Spectroscopy (C-NIRS) detects hemodynamic activation responses more robustly than single-detector NIRS" NeuroImage 55 (2011) 1679-1685 (Year: 2011).*
Gagnon "Short separation channel location impacts the performance of short channel regression in NIRS" NeuroImage 59 (2012) 2518-2528 (Year: 2012).*
Hasan "Suitibility Investigation of the Different Classifiers in fNIRS Signal Classification" 2020 IEEE Region 10 Symposium (TENSYMP) Jun. 5-7, 2020, Dhaka, Bangladesh (Year: 2020).*
Peck H. Koh et al., "Functional optical signal analysis: a software tool for near-infrared spectroscopy data processing incorporating statistical parametric mapping", Journal of Biomedical Optics, 2007, vol. 12, No. 6, pp. 064010-1-064010-13 (13 pages total).
Satoru Kohno et al., "Removal of the skin blood flow artifact in functional near-infrared spectroscopic imaging data through independent component analysis", Journal of Biomedical Optics, 2007, vol. 12, No. 6, pp. 062111-1-062111-9 (9 pages total).
Evgeniya Kirilina et al., "The Physiological origin of task-evoked systemic artefacts in functional near infrared spectroscopy", NeuroImage, 2012, vol. 61, pp. 70-81 (12 pages total).
Theodore J. Huppert et al., "HomER: a review of time-series analysis methods for near-infrared spectroscopy of the brain", Appl Opt., 2009, vol. 48, No. 10, pp. 1-33 (34 pages total).
Theodore J. Huppert, "Commentary on the Statistical properties of noise and its implication on general linear models in functional near-infrared spectroscopy", Neurophotonics, 2016, vol. 3, No. 1, pp. 010401-1-010401-10 (11 pages total).
K.J. Friston et al., "Event-Related fMRI: Characterizing Differential Responses", Neuroimage, 1998, vol. 7, pp. 30-40, Article No. NI970306 (11 pages total).
Sergio Fantini et al., "Perspective: Prospects of non-invasive sensing of the human brain with diffuse optical imaging", APL Photonics., 2018, vol. 3, No. 11, pp. 1-21 (21 pages total).
Solomon Gilbert Diamond et al., "Dynamic physiological modeling for functional diffuse optical tomography", NeuroImage, 2006, vol. 30, pp. 88-101 (14 pages total).
G. Bauernfeind et al., "Separating heart and brain: On the reduction of physiological noise from multichannel functional near-infrared spectroscopy (fNIRS) signals", Journal of Neural Engineering, 2014, vol. 11, No. 5, pp. 1-28 (29 pages total).
Edson Amaro Jr. et al., "Study design in fMRI: Basic principles", Brain and Cognition, 2006, vol. 60, pp. 220-232 (13 pages total).
Guilherne Augusto Zimeo Morais et al., "Non-neuronal evoked and spontaneous hemodynamic changes in the anterior temporal region of the human head may lead to misinterpretations of functional near-infrared spectroscopy signals", Neurophotonics, 2018, vol. 5, No. 1, pp. 011002-1-011002-9 (10 pages total).
Xin Zhou et al., "Comparing fNIRS signal qualities between approaches with and without short channels", PLOS One, 2020, vol. 15. No. 12, pp. 1-18 (18 pages total).
Yiheng Zhang et al., "Eigenvector-based spatial filtering for reduction of physiological interference in diffuse optical imaging", Journal of Biomedical Optics, 2005, vol. 10, No. 1, pp. 011014-1-011014-11 (11 pages total).
Dominik Wyser et al., "Short-channel regression in functional near-infrared spectroscopy is more effective when considering heterogeneous scalp hemodynamics", Neurophotonics, 2020, vol. 7, No. 3, pp. 035011-1-035011-23 (23 pages total).
Sungho Tak et al., "Statistical analysis of fNIRS data: A Comprehensive review", NeuroImage, 2014, vol. 85, pp. 72-91 (20 pages total).
Toshimitsu Takahashi et al., "Influence of skin blood flow on near-infrared spectroscopy signals measured on the forehead during a verbal fluency task", NeuroImage, 2011, vol. 57, pp. 991-1002 (12 pages total).
Ilias Tachtsidis et al., "False Positives in Functional Near-Infrared Topography", Adv Exp Med Biol, 2009, vol. 645, pp. 307-314 (8 pages total).
Ilias Tachtsidis et al.,"False Positives and false negatives in functional near-infrared spectroscopy issues, challenges, and the way forward", Neurophotonics, 2016, vol. 3, No. 3, pp. 031405-1-031405-6 (7 pages total).
Matthias L. Schroeter et al., "Towards a standard analysis for functional near-infrared imaging", NeuroImage, 2004, vol. 21, pp. 283-290 (8 pages total).
Paola Pinti et al., "The present and future use of functional near-infrared spectroscopy (fNIRS) for cognitive neuroscience", Ann. N.Y. Acad. Sci., 2018, pp. 1-25 (25 pages total).
Hellmuth Obrig et al., "Beyond the Visible—Imaging the Human Brain With Light", Journal of Cerebral Blood Flow & Metabolism, 2003, vol. 23, No. 1, pp. 1-18 (18 pages total).
Tiina Nasi et al., "Effect of task-related extracerebral circulation on diffuse optical tomography: experimental data and simulations on the forehead", Biomedical Optics Express, 2013, vol. 4, No. 3, pp. 412-426 (15 pages total).
Isao Nambu et al., "Transient increase in systemic interferences in the superficial layer and its influence on event-related motor tasks: a functional near-infrared spectroscopy study", Journal of Biomedical Optics, 2017, vol. 22, No. 3, pp. 035008-1-035008-11 (12 pages total).
Ludovico Minati et al., "Intra- and extra-cranial effects of transient blood pressure changes on brain near-infrared spectroscopy (NIRS) measurements", Journal of Neuroscience Methods, 2011, vol. 197, pp. 283-288 (6 pages total).
Sheena Luu et al., "Decoding subjective preference from single-trial near-infrared spectroscopy signals", Journal of Neural Engineering, 2009, vol. 6, No. 1, pp. 1-8 (8 pages total).
Alexander von Lühmann et al., "Using the General Linear Model to Improve Performance in fNIRS Single Trial Analysis and Classification: A Perspective", Frontiers in Human Neuroscience, 2020, vol. 14, pp. 1-17 (17 pages total).
S.B. Borgheai et al., "Multimodal exploration of non-motor neural functions in ALS patients using simultaneous EEG-fNIRS recording", Journal of Neural Engineering, 2019, vol. 16, No. 6, pp. 1-15 (15 pages total).
Rand K. Almajidy et al., "A Newcomer's Guide to Functional Near Infrared Spectroscopy Experiments", IEEE Reviews in Biomedical Engineering, 2020, vol. 13, pp. 292-308 (17 pages total).
European Search Report dated Oct. 29, 2021 in European Application No. 21 38 2733.

* cited by examiner

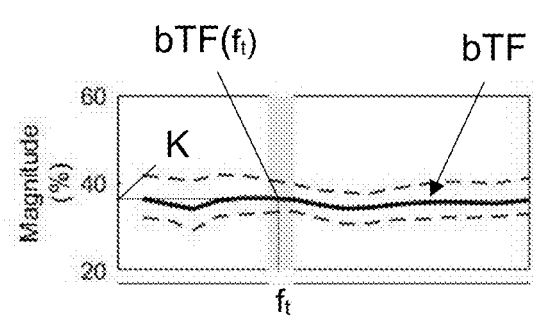 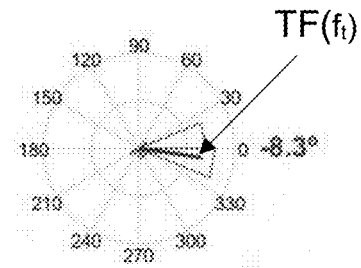
Fig. 5a Fig. 5b
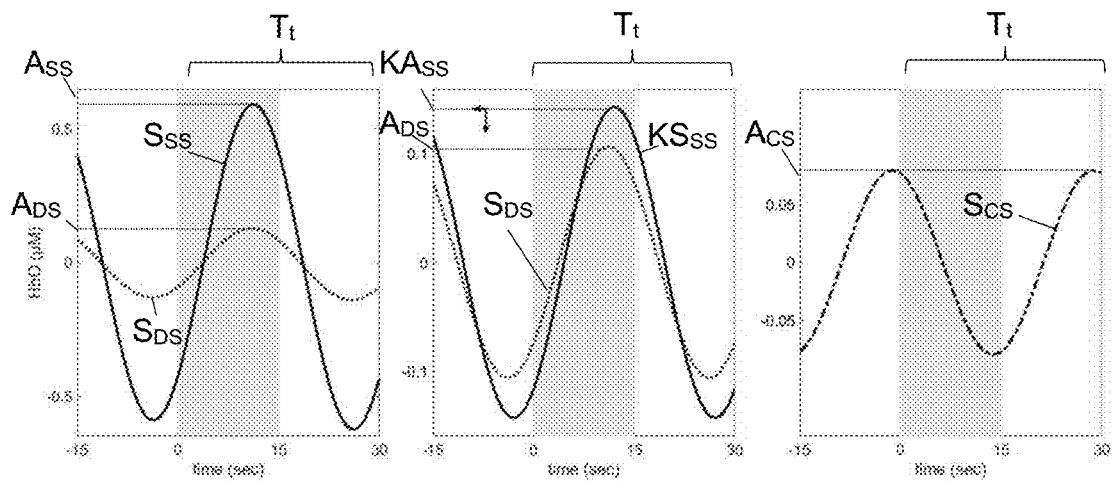
Fig. 6a Fig. 6b Fig. 6c
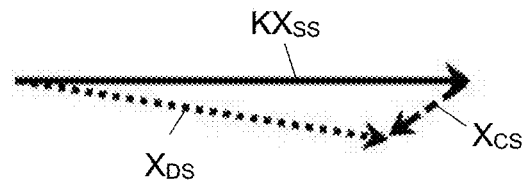
Fig. 7

METHOD FOR OBTAINING NEAR-INFRARED SPECTROSCOPY CEREBRAL SIGNAL

CROSS-REFERENCE TO THE RELATED APPLICATION(S)

This application claims priority under 35 USC § 119 to European Patent Application No. 21382675.3 filed on Jul. 23, 2021 and to European Patent Application No. 21382733.0 filed on Aug. 3, 2021, the contents of which are herein incorporated by reference in their entireties.

BACKGROUND

1. Field

The disclosure relates to a method for obtaining a near-infrared spectroscopy cerebral signal in a subject using a cyclic cerebral stimulation at a given task frequency, where the cerebral signal is clean, not presenting interfering components from other parts of the body, and corresponding mainly to brain activity.

2. Description of the Related Art

Based on the neurovascular coupling principle, functional near-infrared spectroscopy (fNIRS) aims at detecting the hemodynamic changes evoked by neuronal oxygen consumption. NIRS is a non-invasive optical imaging technology, and it has been widely used to measure brain, mostly cortical, activity through relative concentration changes in oxygenated (HbO) and deoxygenated (HbR) hemoglobin (for reviews see: Obrig & Villringer, 2003; Pinti et al., 2018).

A major challenge in fNIRS research is to reliably disentangle the hemodynamic response due to neurovascular coupling from other confounding components (Tachtsidis & Scholkmann, 2016). fNIRS changes caused by brain activity are naturally low in amplitude and unfortunately also overlap with other fluctuations that do not originate in the cerebral cortex, mainly: (i) systemic hemodynamic activity detectable in both cerebral and extracerebral regions (Bauernfeind, Wriessnegger, Daly, & Müller-Putz, 2014; Minati, Kress, Visani, Medford, & Critchley, 2011; Tachtsidis et al., 2009), (ii) local blood flow changes in superficial tissue layers across the head (Kirilina et al., 2012), and (iii) instrumental noise and other artifacts. The first two, far from being simply spontaneously generated, can also be evoked by cognitive, emotional or physical tasks. If the modulation of these non-cortical task-related components of the signal mimics the dynamics of the brain activation of interest they could become an important source of interference and noise (Nambu et al., 2017; Näsi et al., 2013; Zimeo Morais et al., 2017). So much so that Takahashi et al. (2011) showed that the task-related skin blood flow (SBF) changes could explain over 90% of the NIRS signal on a verbal fluency experiment, while Minati et al. (2011) further demonstrated the strong confounding effect of arterial blood pressure (ABP) fluctuations.

To better infer the presence of a functional response, experimental protocols attempt to increase statistical power by repeating the stimuli a sufficient number of times, interspersed with contrast conditions in which a different response (or none) is expected. To this end, fNIRS experiments often used blocked or event-related designs, depending on whether one wants to analyze sustained or transient responses, respectively (Pinti et al., 2018). Event-designs use short-duration stimuli, normally randomized in order and separated by a constant or jittered inter-stimulus interval. Block-designs attempt to maintain mental engagement by presenting stimuli within a condition for a long enough time interval, followed by a different condition or a resting inter-stimulus interval (Amaro & Barker, 2006). To investigate the interaction between 'sustained' and 'transient' responses, mixed designs can also be used ("*The mixed block/event-related design*", Petersen & Dubis, 2012).

Depending on the stimulus presentation strategy, different analysis methods have been developed to make inference about the functional hemodynamic response and isolate it from confounding interferences (for a review see Sungho Tak & Ye, 2014). Although classic averaging strategies provide robust results, the usual averaged-based statistical tests, such as t-test or ANOVA, do not allow estimating the shape or time-course of fNIRS signals, so they have been progressively replaced by more powerful methods. These include the general linear model (GLM) framework ("*Statistical Parametric Mapping: The Analysis of Functional Brain Images*", K. Friston, Ashburner, Kiebel, & Nichols, 2007; Schroeter, BUcheler, et al., 2004), data-driven approaches as principal component analysis (PCA) and independent component analysis (ICA) (Kohno et al., 2007; Yiheng Zhang, Brooks, Franceschini, & Boas, 2005) and dynamic state-space modeling (Diamond et al., 2006; "*State-estimation approach to the nonstationary optical tomography problem*", Kolehmainen, Prince, Arridge, & Kaipio, 2003). GLM is one of the most widely adopted statistical framework to quantify how well the measured fNIRS signals fit a hemodynamic model that reflects the expected neural response. It exploits the good temporal resolution of fNIRS and allows for including different covariates within the regression model (e.g. physiological signals). In its most basic form, the model is obtained by convolving a hemodynamic response function (HRF) with a stimuli function that encodes the hypothesized time course of the neuronal response ("*Functional optical signal analysis: a software tool for near-infrared spectroscopy data processing incorporating statistical parametric mapping*", Koh et al., 2007; Sungho Tak & Ye, 2014). Therefore, GLM is a hypothesis-driven approach that requires the combination of a specific HRF (often taken from fMRI studies) and other nuisance regressors to construct the linear model, which might not be obvious depending on the task type, brain region and participant's idiosyncrasy. Moreover, GLM demands special caution when applied to fNIRS signals due to some statistical issues (Huppert, 2016; Huppert, Diamond, Franceschini, & Boas, 2009; Koh et al., 2007). In contrast, PCA and ICA methods only rely on general statistical assumptions as orthogonality and independence, respectively. Although useful for separating the mixed components that make up the fNIRS signals, they require additional processing to elucidate which of them are task-related and which are not, particularly difficult when extracerebral and cerebral responses are correlated (Zhou, Sobczak, McKay, & Litovsky, 2020). State-space models, mainly based on the Kalman filter, allow building complex hemodynamic models to describe the time varying characteristics of the fNIRS signals and estimate the HRF. Although dynamic analysis appears to provide better estimates of the HRF and better account for non-stationary signals, it still requires improvements in model specifications and state-space estimators.

Regardless of the strengths and weaknesses of each experimental method, all benefit from the inclusion of short-distance recordings to obtain a reference of the superficial layers contribution to fNIRS signals (for reviews see: Fantini, Frederick, & Sassaroli, 2018; Tachtsidis & Scholkmann, 2016; Sungho Tak & Ye, 2014). Multi-distance measurements are considered particularly effective in isolating the actual cerebral response. Nevertheless, some open questions remain regarding, for example, the ideal range for source-detector distances, the optimal number of short-channels and their arrangement relative to long-channels. Ideally, and since there is growing evidence of the heterogeneous nature of surface hemodynamics (Wyser et al., 2020), each long-channel should be paired with at least one nearby short-channel. Unfortunately, such a precise spatial configuration of the paired measurements is not currently possible with the most commonly used NIRS devices today.

It is therefore an objective of the disclosure providing a method to obtain a near-infrared spectroscopy cerebral signal in a subject having only access to long and short channels.

SUMMARY

Example embodiments of the disclosure describe a method for obtaining a near-infrared spectroscopy cerebral signal in a subject. The method according to an example embodiment may include steps of placing a near-infrared emitter and respective proximal and distal near-infrared detectors on the skin of the head of the subject; during a baseline recording stage with the subject in resting-state, recording by a computer near-infrared signals received from the near-infrared emitter in the proximal and distal near-infrared detectors, the recorded signals comprising a baseline deep-signal received by the distal near-infrared detector, and a baseline shallow-signal received by the proximal near-infrared detector; calculating by the computer a scaling factor between the amplitudes of the baseline deep-signal and the baseline shallow-signal at a given task-frequency; with the subject undergoing a cyclic cerebral stimulation at the task-frequency during a stimulation recording stage, recording by the computer near-infrared signals received from the near-infrared emitter in the proximal and distal detectors, the recorded signals comprising a deep-signal received by the distal near-infrared detector, and a shallow-signal received by the proximal near-infrared detector. Then obtaining by the computer the cerebral signal at the task-frequency during stimulation by applying the scaling factor to the shallow-signal; and calculating the cerebral signal at the task-frequency as the difference between the deep-signal and the scaled shallow-signal, at the task-frequency. The steps of the method may be performed by a computer or a data processing apparatus programmed accordingly. The computer may be a single computer comprising software conveniently programmed to perform the steps of the method. Also, embedded devices or distributed computer systems, or other known computer arrangements may be used for carrying out the method, as known by the skilled person.

Advantageously, performing a cyclic cerebral stimulation at a given task frequency such as a cyclic cognitive task would induce periodic hemodynamic fluctuations measurable in fNIRS recordings, therefore an oscillatory state suitable for effective analysis in the frequency-domain may be generated. To this end, mental arithmetic task within a cyclic block-design may be employed at a specific frequency, while performing multi-distance recordings on the forehead.

Previously, surface fluctuations were only considered annoying confounders that need to be remove, but in the disclosure the fluctuations are viewed instead as carriers of valuable information, information that might prove essential not only to gain a better understanding of fNIRS data but also, and perhaps as important, to more precisely assess the full dynamics of the neuro-visceral link, so the cerebral signal may be calculated from the deep-signal and the shallow-signal during cyclic cerebral stimulation at the given task frequency.

Task-related arousal mechanism requires a close interaction between cognitive function and autonomic control ("*Effects of Blood Pressure on Cognitive Performance: A Systematic Review*", Forte, De Pascalis, et al., 2019; "*Heart Rate Variability and Cognitive Function: A Systematic Review*", Forte, Favieri, et al., 2019; "*Autonomic Dysfunction in Mild Cognitive Impairment: Evidence from Power Spectral Analysis of Heart Rate Variability in a Cross-Sectional Case-Control Study*" Nicolini et al., 2014; "*Claude Bernard and the heart-brain connection: Further elaboration of a model of neurovisceral integration*", Thayer & Lane, 2009; "*Cerebral and neural regulation of cardiovascular activity during mental stress*", Wang et al., 2016). Thus, the autonomic control appears to be associated with activity levels in executive brain regions, which allows an adaptive response to environmental demands. Conversely, autonomic dysfunctions may be related to the deterioration of certain cognitive functions, specifically of executive functions (Forte, De Pascalis, et al., 2019; Forte, Favieri, et al., 2019). This close coordination of extracerebral and cerebral responses with the task-frequency may have great functional value. The correct coupling between physiological resources may be the sign of proper cognitive and/or cardiovascular function and, its disruption, a potential early marker of cognitive decline and/or cardiovascular disease. Therefore, the cerebral signal at the task-frequency, and its relation with extracerebral responses, may be useful for the diagnosis and assessment of dementias like Alzheimer's disease; neurodevelopment disorders like autism or ADHD, affective disorders and autonomic dysfunctions, among other clinical entities involving brain functional changes.

According to an embodiment of the disclosure, the cerebral stimulation is a mental or cognitive activity, such as a mental arithmetic task, so the near-infrared spectroscopy cerebral signal corresponds to the cerebral response caused by the mental or cognitive activity.

According to another embodiment of the disclosure, the cerebral stimulation may be a visual, or auditive, or olfactory, or gustative, or somatosensorial, or motor activity, so the near-infrared spectroscopy cerebral signal corresponds to the cerebral responses caused by the corresponding cerebral stimulation.

According to an embodiment of the disclosure, the step of obtaining the cerebral signal at the task-frequency during stimulation comprises obtaining by the computer the phase, it is, the phase angle, and amplitude of the cerebral signal. As the cerebral signal is expected to have a frequency equal to the task-frequency, the components required for obtaining the cerebral signal are its amplitude and phase, as the frequency is already known. Therefore, the difference between the deep-signal and the scaled shallow-signal, filtered at the task-frequency, would provide the phase, it is, the phase angle, and amplitude of the cerebral signal.

According to an embodiment of the disclosure, the step of obtaining by the computer the phase and amplitude of the cerebral signal during stimulation comprises: determining by the computer a deep-signal phasor corresponding to the deep-signal during stimulation at the task-frequency, having: phase: the phase difference between the deep-signal and the shallow-signal at the task-frequency, and amplitude: the amplitude of the shallow-signal at the task-frequency; determining by the computer a shallow-signal phasor corresponding to the shallow-signal during stimulation at the task-frequency, having a reference phase (for example 0°), and an amplitude of the shallow-signal at the task-frequency, multiplied by the scaling factor; determining by the computer a cerebral-signal phasor by subtracting the shallow-signal phasor from the deep-signal phasor, it is, calculating their difference; and calculating by the computer the phase and amplitude of the estimated cerebral signal at the task-frequency. Advantageously, since the significant components of the frequency of the shallow-signal and the deep-signal are found to be at a frequency equal to the task-frequency, the cerebral signal may be obtained by appropriately combining phasors at the task-frequency derived from the shallow-signal and the deep-signal.

According to an embodiment of the disclosure, the phase difference between the deep-signal and the shallow-signal at the task-frequency is obtained by calculating by the computer an empirical transfer function in the frequency domain between the deep-signal and the shallow-signal and calculating by the computer the argument of the transfer function at the task-frequency, therefore an empirical transfer function may be used to estimate by the computer the phase of the cerebral signal, corresponding to the functional brain activity, by obtaining the timed-coordination between extracerebral and cerebral responses.

According to an embodiment of the disclosure, the step of calculating by the computer a scaling factor between the amplitudes of the basal deep-signal and the basal shallow-signal at the task-frequency comprises calculating by the computer an approximation of a complex frequency dependent basal transfer function between the basal deep-signal and the basal shallow-signal and determine by the computer the scaling factor as the gain of the basal transfer function at the task-frequency, therefore an empirical transfer function may also be used by the computer to estimate the gain of the functional brain activity, which may be applied for obtaining the cerebral signal. Therefore, both gain or amplitude and phase of the cerebral signal may be obtained by the computer using a transfer function applied to the deep-signal and shallow-signal.

According to an embodiment of the disclosure, the task-frequency is a frequency between 0.015 Hz and 0.07 Hz, so natural oscillations of the body, such as the oscillations caused by heart beating, breathing or Mayer arterial pressure waves does not affect the cerebral signal. In an embodiment, the task-frequency is a frequency between 0.025 Hz and 0.05 Hz, such that the task-frequency is far enough from the known natural oscillations of the body. More In an embodiment, the task-frequency is a frequency of 0.033 Hz, such that the corresponding period is 15 seconds, which may be easily measured for computing the duration of each period during the cyclic cerebral stimulation.

According to an embodiment of the disclosure, having a plurality of groups of near-infrared emitter and respective proximal and distal near-infrared detectors, grouped by regions of interest, the method further comprises averaging determine by the computer the shallow-signal and the deep-signal obtained for each group, so the signals are averaged, reducing the signal-noise ratio for each region of interest.

According to an embodiment of the disclosure, the step of the recording during a stimulation comprises alternating semi-periods of stimulating in the subject a cyclic mental task; and semi-periods of baseline resting, such that the task-frequency is maintained during the recording phase, allowing to promote the components of the deep-signal and shallow-signal at the task-frequency. Therefore, it is also expected that the semi-periods of stimulating and the semi-periods of baseline resting have the same duration.

A system to obtain a near-infrared spectroscopy cerebral signal in a subject is also disclosed, the system comprising a device comprising a near-infrared emitter and respective proximal and distal near-infrared detectors, adapted for placing the near-infrared emitter and respective proximal and distal near-infrared detectors on the skin of the head of the subject; and a computer comprising means for carrying out the steps of: during a baseline recording stage with the subject in resting-state, record near-infrared signals received from the near-infrared emitter in the proximal and distal near-infrared detectors, the recorded signals comprising a baseline deep-signal received by the distal detector, and a baseline shallow-signal received by the proximal detector; calculate a scaling factor between the amplitudes of the baseline deep-signal and the baseline shallow-signal at a given task-frequency; with the subject undergoing a cyclic cerebral stimulation at the task-frequency during a stimulation recording stage, record near-infrared signals received from the near-infrared emitter in the proximal and distal detectors, the recorded signals comprising: a shallow-signal received by the proximal detector, and a deep-signal received by the distal detector; obtaining the cerebral signal at the task-frequency during stimulation by applying the scaling factor to the shallow-signal; and calculating the cerebral signal at the task-frequency as the difference between the deep-signal and the scaled shallow-signal, at the task-frequency. The difference between the deep-signal and the scaled shallow-signal, at the task-frequency, may be calculated by the computer as the difference of phasors of the deep-signal and the scaled shallow-signal at the task-frequency, so the phase and amplitude of the cerebral signal may be calculated by the computer in a non-invasive way.

BRIEF DESCRIPTION OF THE DRAWINGS

As a complement to the description provided herein and for the purpose of helping to make the characteristics of the disclosure more readily understandable, this specification is accompanied by a set of drawings, which by the way of illustration and not limitation, represent the following:

FIG. 5a presents the gain of a transfer function between the filtered signals of the shallow and deep channels during the baseline recording stage of FIG. 4;

FIG. 5b presents the phase of a transfer function between the filtered signals of the shallow and deep channels during the stimulation recording stage of FIG. 4;

FIG. 6a presents the averaged periods of the shallow signal and deep signal of FIG. 4 during the stimulation recording stage;

FIG. 6b presents the scaled shallow signal and the deep signal of FIG. 6a;

FIG. 6c presents the obtained cerebral signal as the difference between the scaled shallow signal and the deep signal of FIG. 6b;

FIG. 7 presents obtaining the cerebral signal as the difference between the scaled shallow signal and the deep signal using phasors;

DETAILED DESCRIPTION

Figure 1:
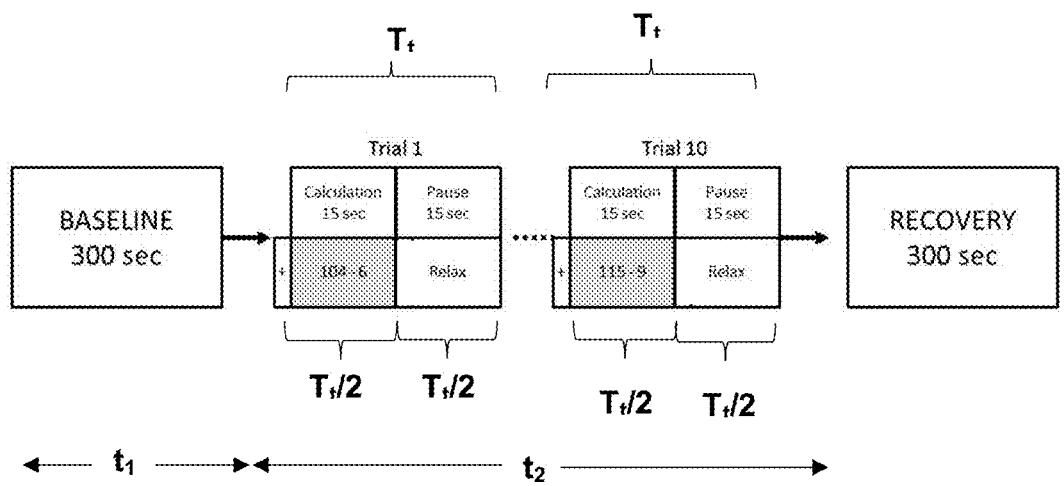
FIG. 1 presents an example of a cerebral stimulation for a given task frequency.

FIG. 1 presents an example of a cyclic cerebral stimulation at a given task-frequency ft that may be used for obtaining the near-infrared spectroscopy fNIRS cerebral signal SCS in a subject 1 using the method of the disclosure through a system 100 comprising a device 10 and a computer 20 adapted to perform the steps of the method.

The cerebral stimulation is a mental or cognitive activity, so the corresponding obtained cerebral signal SCS will be related to this mental or cognitive activity. FIG. 1 presents a cyclic cerebral stimulation at a given task frequency ft is based on a block protocol designed as a cyclical pattern of mental effort, alternating semi-periods Tt/2 of mental math, with semi-periods Tt/2 of pause, of the same duration, i.e. regular repetitions of activation-rest, The idea behind this is to induce periodic hemodynamic changes in the form of cycles of some kind of response to the subject 1 followed by a return to basal levels. In this way, such an oscillatory pattern may be analyzed by conventional spectral methods. This cyclical cerebral estimulation may also be programmed in a computer.

As illustrated in FIG. 1, the cyclic cerebral stimulation is organized into three consecutive uninterrupted recordings: (i) 300 seconds of baseline in resting condition, as baseline recording stage t1 (ii) 300 seconds of mental artihmetic task, as stimulation recording stage t2 and (iii) 300 seconds of recovery in a relaxed state. In this case, the stimulation recording stage t2 consist of 10 consecutive 30-second trials, with a 30 second period Tt. Each trial began with a semi-period Tt/2 of 15 seconds of mental calculation, followed by a semi-period Tt/2 of 15-second pause of relaxation. To perform the mental math participants were asked to iteratively subtract a small number (between 5 and 9) from a three-digit number (between 100 and 199), as fast as possible. Both numbers, chosen randomly in each trial, were presented on a 21.5" display monitor, 80 cm. away from the participants' eyes. Afterwards, the pause started by presenting the question "Result?" for 5 seconds, which prompted the participants to inform verbally of the final result of their mental calculations (to allow scoring the performance and ensuring that the participants were paying attention), followed by a soft image during which the participants were instructed to relax. Two seconds before presenting the subtraction operands, a fixation cross was displayed in the middle of the computer screen to announce the beginning of the mental calculation. Further, during the stimulation recording stage t2 the importance of making a mental effort was constantly emphasized, and not the amount or accuracy of the operations performed.

In this case, the 30-second period of the mental arithmetic trials corresponds to a task-frequency $f_t$ of 0.033 Hz. This frequency was chosen so that it did not overlap with well know spontaneous fluctuations such as ABP (0.08-0.12 Hz), or very slow endothelial activity (0.01-0.02 Hz). Furthermore, the 15-second duration of mental effort accommodates that of a typical hemodynamic response, while the next 15-second pause allows a return to baseline levels, being an optimal inter-event interval to minimize overlaps between consecutive hemodynamic responses. However, other task-frequency $f_t$ are also envisaged, for example frequencies between 0.015 Hz and 0.07 Hz, and frequencies between 0.025 Hz and 0.05 Hz may also be used.

In this case the cyclic cerebral stimulation is a mental arithmetic task, it is, a mental or cognitive activity, so the cerebral signal $S_{CS}$ to be obtained will be a response of the subject 1 to such mental or cognitive activity. However, in other embodiments, it is envisaged that the cerebral stimulation may be a visual, or auditive, or olfactory, or gustative or somatosensorial or motor activity, or even other activities depending on the cerebral signal $S_{CS}$ to be obtained as a response of the subject 1.

Figure 2:
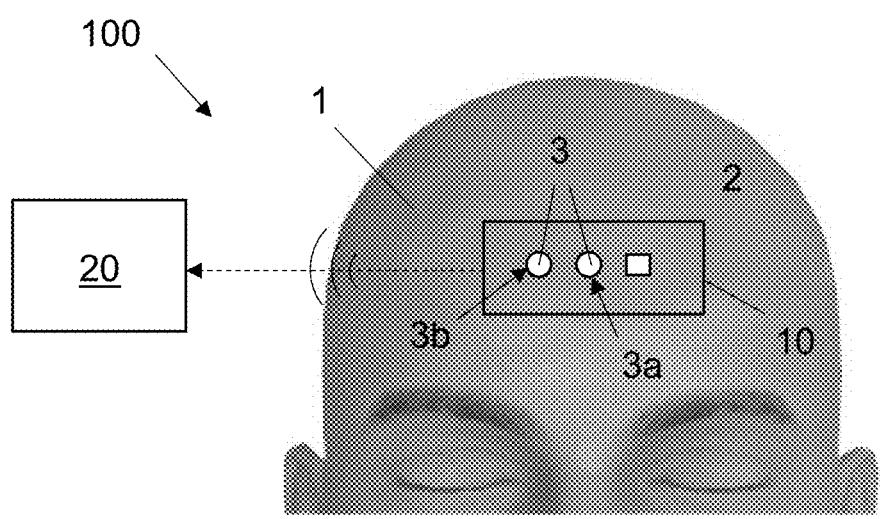
FIG. 2 presents an example of the placement of an emitter and respective proximal and distal detectors on the skin of the head of a subject.

As shown in FIG. 2, for obtaining a near-infrared spectroscopy (fNIRS) cerebral signal $S_{CS}$ in a subject 1 a near-infrared emitter 2 and two detectors 3, respectively a proximal detector 3a and a distal detector 3b, mounted on a device 10 of the system 100, are placed on the skin of the head of the subject 1, typically in the fronto-polar region. It will allow obtaining the near-infrared spectroscopy (fNIRS) cerebral signal $S_{CS}$ in the subject 1 during cyclic cerebral stimulation at the given task frequency $f_t$.

The proximal detector 3a is placed closer to the emitter 2 than the distal detector 3b, for example, the proximal detector 3a is placed 14 mm from the emitter 2 and the distal detector 3b is placed 32 mm from the emitter 2. Naturally, other arrangements of various emitters 2 and detectors 3 in the device 10 are also possible and they may be used for obtaining the near-infrared spectroscopy cerebral signal $S_{CS}$ in the subject 1 in a similar way as explained hereinafter.

The wavelength of the emitter 2 and detectors 3 will be adapted to detect the differences caused by the cerebral stimulation. For example, a near-infrared wavelength of 740 and 850 nm would be suitable for detecting relative changes in oxyhemoglobin (HbO) and deoxyhemoglobin (HbR) concentration, consequently the cerebral signal obtained would be proportional to the adsorption of the emitted and received wavelengths.

Figure 3:
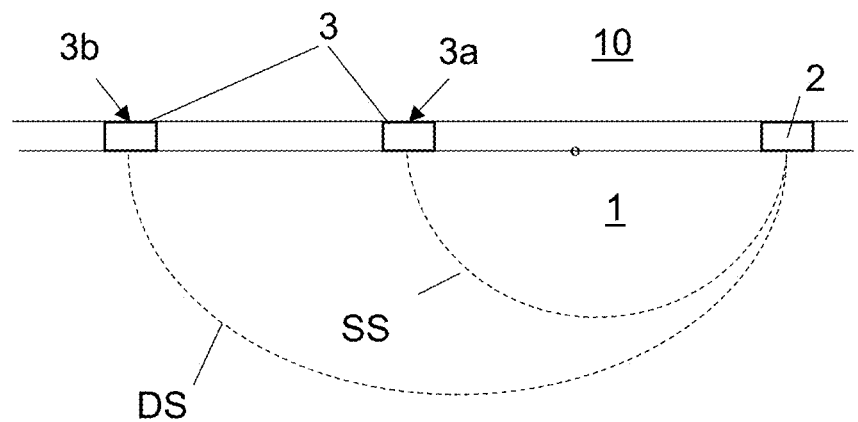
FIG. 3 presents a schema of the shallow and deep channels between the emitter and detectors of FIG. 2.

FIG. 3, shows a representation of the shallow channel SS established between the emitter 2 and the proximal detector 3a and the deep channel DS established between the emitter 2 and the distal detector 3b. The emitter 2 may be a light emitting diode emitting the wavelength of interest, in this case, a wavelength of 850 nm, and the detectors 3 may be fotodiodes or fototransistors, also known as optodes, adapted to receive the wavelength of interest and generating a corresponding electrical signal, that will be transmitted, for example wirelessly, and processed by a computer 20 of the system 100.

FIGS. 4 to 7 are related to a method for obtaining a cerebral signal $S_{CS}$ by a computer 20 based on detected changes in oxyhemoglobin (HbO), but other cerebral signals based on detected changes in other components at other wavelengths, such as deoxyhemoglobin (HbR) or even total hemoglobin (HbT) or isobestic point at 804-805 nm where the adsorption caused by HbO and HbR is the same may be used. Therefore, other wavelengths may be emitted or received as needed, depending on the variation of the component to be detected for obtaining the corresponding cerebral signal.

Figure 4:
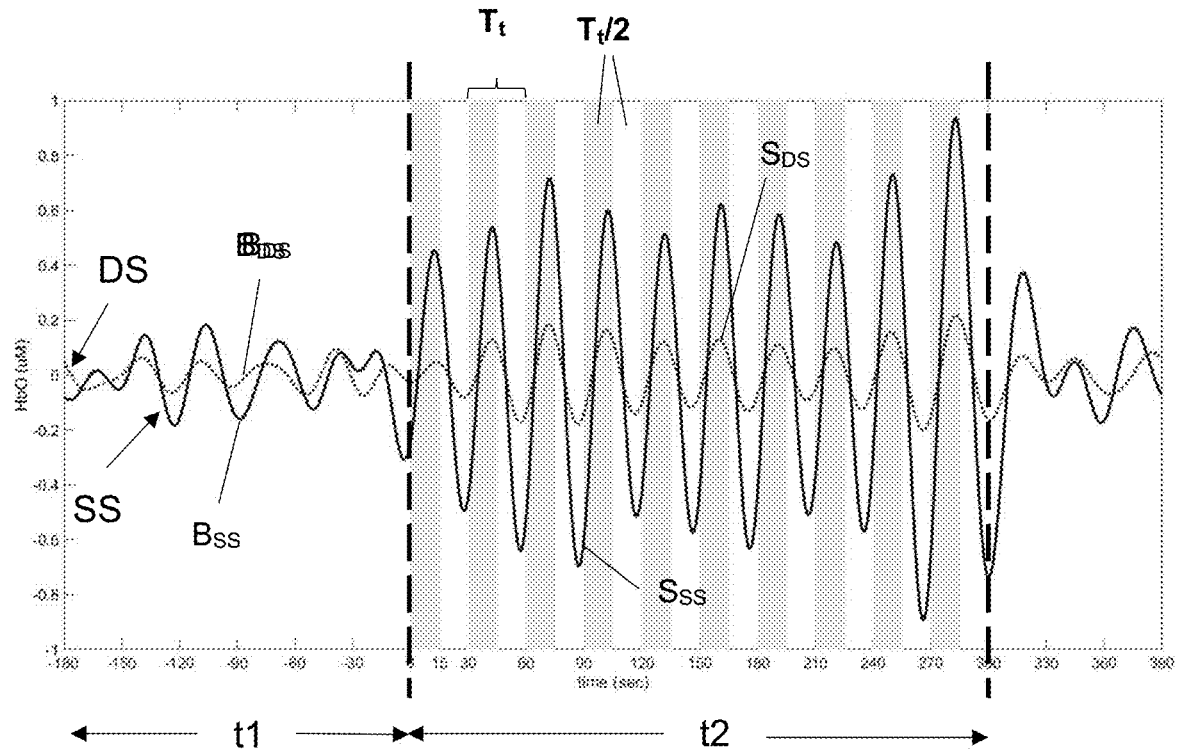
FIG. 4 presents a recording of filtered signals of the shallow and deep channels at the given task-frequency during the baseline and stimulation recording phase of the cerebral stimulation of FIG. 1

FIG. 4 shows an example of a recording of signals from the shallow channel SS and deep channel DS during the baseline recording stage $t_1$ with the subject in resting-state and the stimulation recording stage t2, which are recorded by the computer 20 As previously explained, the stimulation recording stage t2 comprises alternating semi-periods Tt/2 of stimulating in the subject 1 the mental task, and semi-periods Tt/2 of baseline resting, where the subject 1 recovers of the mental task, the semi-periods Tt/2 of stimulating and the semi-periods Tt/2 of baseline resting have the same duration. Advantageously, combining semi-periods Tt/2 of stimulating and the semi-periods Tt/2 of baseline resting induces a cyclic cerebral stimulation at the given task frequency $f_r$.

The signals presented in FIG. 4 have been adapted and filtered by the computer 20 around the task-frequency $f_r$ so components of the signals at the same task-frequency $f_r$ are obtained. In this case, the raw optical data of each detector 3 was converted to optical density, and then into oxyhemoglobin (HbO) and deoxyhemoglobin (HbR) relative concentration changes via the modified Beer-Lambert law, in this case only oxyhemoglobin (HbO) relative concentration is presented for illustrative purposes. The data was digitally band-filtered by the computer 20 around the task-frequency $f_r$, in this case using a zero-phase filter with a filter width of 0.015 Hz, other filtering and filter widths may be used for obtaining the signals around the task-frequency $f_r$ without introducing a delay, or compensating such delay.

As it can be seen in FIG. 4, during the baseline recording stage $t_1$ with the subject in resting-state, near-infrared signals received from the near-infrared emitter 2 in the proximal and distal near-infrared detectors 3 at the task-frequency $f_r$ were recorded by the computer 20, the recorded signals comprising a baseline deep-signal $B_{DS}$ received by the distal near-infrared detector, and a baseline shallow-signal $B_{SS}$ received by the proximal near-infrared detector.

During the stimulation recording stage t2, with the subject undergoing a cyclic cerebral stimulation at the task-frequency $f_r$ according to the pattern of FIG. 1, near-infrared signals received from the near-infrared emitter 2 in the proximal and distal near-infrared detectors 3 at the task-frequency $f_r$ were recorded by the computer 20, the recorded signals comprising a shallow-signal $S_{SS}$ received by the proximal detector 3a, and a deep-signal $S_{DS}$ received by the distal detector 3b.

Since fNIRS signals are dominated by confounding hemodynamics not originated in the cerebral cortex by functional activity, but with origin in blood flow changes in superficial tissues and by changes in systemic physiology that are present both in the superficial layers and in the brain tissue itself, even at different time scales. To address this issue, an effective strategy is the use of multi-distance measurements. Shallow components are removed from the deep-signals by assuming that short-separation recordings are sensitive only to extra-cerebral changes while long-separation recordings are sensitive to both extra-cerebral and cerebral activity.

Therefore, at the task-frequency $f_r$ removing shallow components present in the shallow-signal $S_{SS}$ from the deep-signal $S_{DS}$ for obtaining the cerebral signal $S_{CS}$ may be expressed by the following linear combination:

$$S_{CS}=S_{DS}-(KS_{SS})$$

Since these signals at the task-frequency $f_r$ are considered to be sinusoids, only their amplitude and phase would differ.

The scaling factor K may be calculated by the computer 20 as the ratio of amplitudes between the baseline deep-signal $B_{DS}$ and the baseline shallow-signal BSS at the task-frequency $f_r$. Multiple other methods are known for calculating by a computer this scaling factor K as the ratio of amplitudes of the baseline deep-signal $B_{DS}$ and the baseline shallow-signal $B_{SS}$, such as detecting the average peak to peak ratio between the baseline deep-signal $B_{DS}$ and the baseline shallow-signal $B_{SS}$, or the ratio between the root mean square measurements of the baseline deep-signal $B_{DS}$ and the baseline shallow-signal $B_{SS}$.

Also, a transfer function strategy may be used by the computer 20 for calculating the scaling factor K, as transfer function models have become a popular approach to investigate the dynamic of cerebrovascular autoregulation ("*Transfer function analysis of dynamic cerebral autoregulation: A white paper from the International Cerebral Autoregulation Research Network*" Claassen et al., 2015; "*Cerebral autoregulation: An overview of current concepts and methodology with special focus on the elderly*", Van Beek, Claassen, Rikkert, & Jansen, 2008), and they have also been used to remove systemic physiological noise from fNIRS signals ("*Physiological Noise Removal from fNIRS Signals*", Bauernfeind, Bock, Wriessnegger, & Müller-Putz, 2013; "*Elimination von Atmungseffekten auf bewegungsinduzierte Änderungen der Herzrate—Elimination of Respiratory Effects on Movement-induced Cardiac Response*",Florian & Pfurtscheller, 1997). Assuming that the shallow-signal $S_{SS}$ has energy in the frequency range of interest, around the task-frequency $f_r$, and contain quasi-periodic oscillations, the transfer function H(f) may be approximated from the experimental fNIRS data as ("*Transfer function analysis of dynamic cerebral autoregulation in humans*", Zhang et al., 1998):

$$H(f) = \frac{CPSD_{ssds}(f)}{PSD_{ss}(f)}$$

For the time-series pair, shallow-signal $S_{SS}$ and deep-signal $S_{DS}$ are, respectively, the input and output signals used to obtain an approximation of the transfer function at the task-frequency $f_r$. From the complex-valued result, we obtained the magnitude (gain), corresponding to the scaling factor K which represents the relative change in μM between input and output, and the phase that carries their temporal coupling (phase difference or time-lag). For reporting the gain, data were converted by the computer 20 into percentage values, which will be the scaling factor K. Then, the scaling factor K may be considered the gain value of the basal transfer function bTF at $f_r$ during "baseline", it is, during the baseline recording stage $t_1$, which represents the fraction of the magnitude of the shallow-signal $S_{SS}$ present in the deep-signal $S_{DS}$ when no significant cerebral signal $S_{CS}$ component contributes.

Therefore, during the step of calculating the scaling factor K between the amplitude of the basal deep-signal Bps and the basal shallow-signal $B_{SS}$ at the task-frequency $f_r$, an approximation of a complex frequency dependent basal transfer function bTF between the basal deep-signal $B_{DS}$ and the basal shallow-signal $B_{SS}$ may be computed by the computer 20 to determine the scaling factor K as the gain of the basal transfer function bTF at the task-frequency $f_r$, as shown in FIG. 5a.

The phase difference between the deep-signal SDS and the shallow-signal $S_{SS}$ at the task-frequency $f_r$ may be obtained by determining by the computer 20 the delay between the deep-signal $S_{DS}$ and the shallow-signal $S_{SS}$ filtered at task-frequency $f_t$ as known by the skilled person, However, this phase difference may also be obtained by calculating an empirical transfer function TF in the frequency domain between the deep-signal $S_{DS}$ and the shallow-signal $S_{SS}$ during the stimulation recording stage t2 and calculating by the computer 20 the argument of the transfer function TF at the task-frequency $f_t$, which is illustrated in FIG. 5b. Therefore, the scaling factor K and the phase difference that will be used to calculate the cerebral signal $S_{CS}$ are obtained.

FIG. 6a shows an averaged period of the periods of the deep-signal $S_{DS}$ and the shallow-signal $S_{SS}$, while FIG. 6b shows the signals of FIG. 6a where the scaling factor K has been applied by the computer 20 to the shallow-signal $S_{SS}$, thus reducing its amplitude.

Then, given the linear combination between the deep-signal $S_{DS}$ and the shallow-signal $S_{SS}$ for obtaining the cerebral signal $S_{CS}$ previously explained, the cerebral signal $S_{CS}$ at the task-frequency $f_t$ may be calculated by the computer 20 as the difference, in phase and amplitude, between the deep-signal $S_{DS}$ and the scaled shallow-signal $KS_{SS}$, at the task-frequency $f_t$, thus obtaining the cerebral signal $S_{CS}$ depicted in FIG. 6c.

Advantageously, since the deep-signal $S_{DS}$ and the shallow-signal $S_{SS}$ are sinusoidal signals with frequency the task-frequency $f_t$, the deep-signal $S_{DS}$ and the shallow-signal $S_{SS}$ may be expressed as a respective phasor vectors corresponding to a deep-signal phasor XDS and shallow-signal phasor $X_{SS}$, having the amplitudes and phases of their corresponding sinusoidal signals, so the linear combination previously indicated may also be expressed as a linear combination of phasors as indicated below:

$$S_{CS} = S_{DS} - (KS_{SS})$$

$$A_{CS} \cos(2\pi f_t t + \phi_{CS}) = A_{DS} \cos(2\pi f_t t + \phi_{DS}) - KA_{SS} \cos(2\pi f_t t + \phi_{SS})$$

$$A_{CS} e^{j\phi_{CS}} = A_{DS} e^{j\phi_{DS}} - KA_{SS} e^{j\phi_{SS}}$$

$$X_{CS} = X_{SD} - KX_{SS}$$

It is expected for one of the phases between the phase of the shallow-signal $\phi_{SS}$ and the phase of the deep-signal $\phi_{DS}$ to be a reference phase, typically a 0 degrees reference phase. In this case, the reference phase of 0 degrees is assigned to the phase of the shallow-signal $\phi_{SS}$.

This way, the difference, in phase and amplitude, between the deep-signal $S_{DS}$ and the scaled shallow-signal $KS_{SS}$ may directly be calculated by the computer 20 as a phasor subtraction of the deep-signal phasor XDS minus the shallow-signal phasor $X_{SS}$ as graphically represented in FIG. 7, for obtaining a cerebral signal phasor $X_{CS}$ with an amplitude and phase corresponding to the amplitude and phase of the cerebral signal $S_{CS}$ at the task-frequency $f_t$.

Therefore, the step of obtaining the phase and amplitude of the cerebral signal $S_{CS}$ during stimulation comprises determining by the computer 20 a deep-signal phasor XDS corresponding to the deep-signal $S_{DS}$ during stimulation at the task-frequency $f_t$, having as phase the phase difference between the deep-signal $S_{DS}$ and the shallow-signal $S_{SS}$ at the task-frequency $f_t$, and amplitude the amplitude of the deep-signal $S_{DS}$ at the task-frequency $f_t$; and determining a shallow-signal phasor $X_{SS}$ corresponding to the shallow-signal $S_{SS}$ during stimulation at the task-frequency $f_t$, having a reference phase of 0 degrees, and as amplitude the amplitude of the shallow-signal $S_{SS}$ at the task-frequency $f_t$, multiplied by the scaling factor K. Naturally, alternatively the reference phase of 0 degrees may be the phase of the deep-signal phasor XDs, or the reference phase may be any known phase, as only the phase difference is relevant.

Then, the phase and amplitude of the estimated cerebral signal $S_{CS}$ at the task-frequency $f_t$ may be calculated by the computer 20 by determining a cerebral-signal phasor $X_{CS}$ by directly subtracting the shallow-signal phasor XDS from the deep-signal phasor XDS, as graphically represented in FIG. 7.

Figure 8:
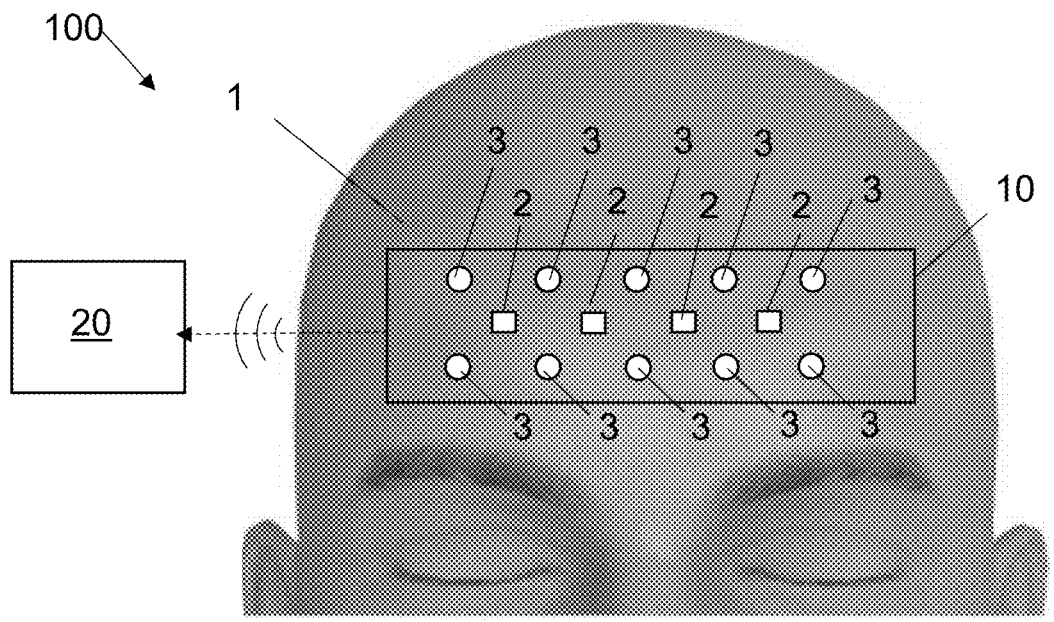
FIG. 8 presents another example of the placement of emitters and respective proximal and distal detectors on the skin of the head of a subject.
Figure 9:
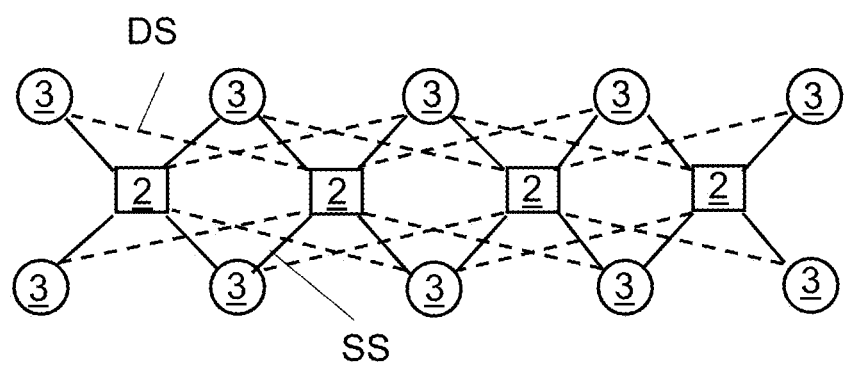
FIG. 9 presents a schema of the shallow and deep channels between the emitters and detectors of FIG. 8.

Although previously only one emitter 2 and a proximal detector 3a and distal detector 3b group was used, also other multichannel, wireless, continuous-wave NIRS device 10 may be used, such as the Brainspy 28, from Newmanbrain, S.L., which employs four emitters 2 and ten detectors 3 forming a rectangular grid of 80×20 mm. In this case, each emitter 2 housed two light-emitting-diodes (LED) at wavelengths 740 nm and 850 nm. Through a precise switching cycle, the device 10 combines pairs of optodes at different separation distances, providing 16 short-channels or shallow channels SS and 12 long-channels or deep channels DS that corresponds to a source-detector distance of 14 and 32 mm respectively, as shown in FIG. 8 and in more detail in FIG. 9. Moreover, it is also expected that the device 10 may measure and correct the ambient light contribution, and it may also it incorporate a 3-axis accelerometer to account for head motion. Data may be wirelessly transmitted (for example via Bluetooth) at a sample rate of 10 Hz to the computer 20, that would execute the steps of processing the data to obtain the near-infrared spectroscopy fNIRS cerebral signal $S_{CS}$.

As shown in FIG. 8, the NIRS probe may be applied onto the forehead, centered on AFpz according to the international 10-5 system, mainly covering the frontopolar area of the prefrontal cortex (PFC). It is expected that the optodes contact the skin through an intermediate convex lens pressing the skin when the probe is held firmly, in order to reduce cutaneous blood flow and, therefore, its hemodynamic interference.

Advantageously, by having a plurality of groups of near-infrared emitter and respective proximal and distal near-infrared detectors grouped by regions of interest, the shallow-signal and the deep-signal obtained for each region may be averaged, so the signal-noise ratio for each region of interest is improved, and a better cerebral signal $S_{CS}$ may be obtained per each region of interest.

While the present disclosure has been described with reference to example embodiments thereof, it will be apparent to those of ordinary skill in the art that various changes and modifications may be made thereto without departing from the spirit and scope of the present disclosure as set forth in the following claims and their equivalents.

The invention claimed is:

1. A method to obtain a near-infrared spectroscopy (fNIRS) cerebral signal in a subject, the method comprising:
   placing a near-infrared emitter, a first near-infrared detector, and a second near-infrared detector on a skin of a head of a subject, the first near-infrared detector being placed closer to the near-infrared emitter than the second near-infrared detector;
   during a baseline recording stage with the subject in resting-state, recording, by a computer, near-infrared signals received from the near-infrared emitter in the first and second near-infrared detectors, the recorded signals comprising:
   a baseline deep-signal received by the second near-infrared detector, and
   a baseline shallow-signal received by the first near-infrared detector;

calculating, by the computer, a scaling factor between amplitudes of the baseline deep-signal and the baseline shallow-signal at a given frequency;

with the subject undergoing a cyclic cerebral stimulation according to an activity that occurs at the given frequency during a stimulation recording stage, recording, by the computer, near-infrared signals received from the near-infrared emitter in the first and second near-infrared detectors, the recorded signals comprising:

a shallow-signal received by the first near-infrared detector, and a deep-signal received by the second near-infrared detector;

obtaining, by the computer, a cerebral signal at the given frequency during stimulation by:

applying the scaling factor to the shallow-signal; and calculating the cerebral signal at the given frequency as a difference between the deep-signal and the scaled shallow-signal, at the given frequency.

2. The method according to claim 1, wherein the cyclic cerebral stimulation is according to a mental or cognitive activity.

3. The method according to claim 1, wherein the cyclic cerebral stimulation is according to a visual, auditive, olfactory, gustative, somatosensorial or motor activity.

4. The method according to claim 1, wherein the obtaining the cerebral signal comprises obtaining, by the computer, a phase and an amplitude of the cerebral signal.

5. The method according to claim 4, wherein the obtaining the phase and the amplitude of the cerebral signal during stimulation comprises:

determining, by the computer, a deep-signal phasor corresponding to the deep-signal during stimulation at the given frequency, having:

a phase difference between the deep-signal and the shallow-signal at the given frequency, and an amplitude of the deep-signal at the given frequency;

determining, by the computer, a shallow-signal phasor corresponding to the shallow-signal during stimulation at the given frequency, having:

a reference phase, and an amplitude of the shallow-signal at the given frequency, multiplied by the scaling factor;

determining, by the computer, a cerebral-signal phasor by subtracting the shallow-signal phasor from the deep-signal phasor; and calculating, by the computer, the phase and amplitude of the estimated cerebral signal at the given frequency.

6. The method according to claim 5, wherein the phase difference between the deep-signal and the shallow-signal at the given frequency is obtained by calculating, by the computer, an empirical transfer function in a frequency domain between the deep-signal and the shallow-signal and calculating, by the computer, an argument of the transfer function at the given frequency.

7. The method according to claim 1, wherein the calculating the scaling factor comprises calculating, calculating, by the computer, an approximation of a complex frequency dependent basal transfer function between the baseline deep-signal and the baseline shallow-signal and determining, by the computer, the scaling factor as a gain of the basal transfer function at the given frequency.

8. The method according to claim 1, wherein the given frequency is a frequency between 0.015 Hz and 0.07 Hz.

9. The method according to claim 1, wherein the given frequency is a frequency between 0.025 Hz and 0.05 Hz.

10. The method according to claim 1, wherein the given frequency is a frequency of 0.033 Hz.

11. The method according to claim 1, wherein a plurality of groups, each including a near-infrared emitter, a first near-infrared detector, and a second near-infrared detector, are provided, and the method further comprises averaging, by the computer, the shallow-signal and the deep-signal obtained for each group.

12. The method according to claim 1, wherein the recording during the stimulation recording stage comprises alternating:

semi-periods of stimulating in the subject; and semi-periods of baseline resting.

13. The method according to claim 12, wherein the semi-periods of stimulating and the semi-periods of baseline resting have the same duration.

14. A system for obtaining a near-infrared spectroscopy (fNIRS) cerebral signal in a subject, the system comprising:

a device comprising a near-infrared emitter, a first near-infrared detector, and a second near-infrared detector, adapted for placing the near-infrared emitter and the first and second near-infrared detectors on a skin of a head of a subject, the first near-infrared detector being placed closer to the near-infrared emitter than the second near-infrared detector; and a computer configured to perform:

during a baseline recording stage with the subject in resting-state, record near-infrared signals received from the near-infrared emitter in the first and second near-infrared detectors, the recorded signals comprising:

a baseline deep-signal received by the second near-infrared detector, and a baseline shallow-signal received by the first near-infrared detector;

calculate a scaling factor between amplitudes of the baseline deep-signal and the baseline shallow-signal with respect to a task that occurs at a given frequency;

with the subject undergoing a cyclic cerebral stimulation according to an activity that occurs at the given frequency during a stimulation recording stage, record near-infrared signals received from the near-infrared emitter in the first and second near-infrared detectors, the recorded signals comprising:

a shallow-signal received by the first near-infrared detector, and a deep-signal received by the second near-infrared detector;

obtaining a cerebral signal at the given frequency during stimulation by:

applying the scaling factor to the shallow-signal; and calculating the cerebral signal at the given frequency as a difference between the deep-signal and the scaled shallow-signal, at the given frequency.

15. The method according to claim 1, further comprising:

obtaining a relation of the cerebral signal and an extra-erebral response; and using the cerebral signal and the relation for diagnosis and assessment of a clinical entity involving a brain functional change.

16. The method according to claim 15, wherein the clinical entity involving the brain functional change comprises at least one of dementia; a neurodevelopment disorder; an affective disorder and an autonomic dysfunction.

* * * * *